(12) United States Patent
Abt

(10) Patent No.: US 11,612,317 B2
(45) Date of Patent: Mar. 28, 2023

(54) OPHTHALMIC SURGERY USING LIGHT-FIELD MICROSCOPY

(71) Applicant: Alcon Inc., Fribourg (CH)

(72) Inventor: Niels A. Abt, Winterthur (CH)

(73) Assignee: Alcon Inc., Fribourg (CH)

( * ) Notice: Subject to any disclaimer, the term of this patent is extended or adjusted under 35 U.S.C. 154(b) by 243 days.

(21) Appl. No.: 17/001,596

(22) Filed: Aug. 24, 2020

(65) Prior Publication Data

US 2020/0383569 A1 Dec. 10, 2020

Related U.S. Application Data

(62) Division of application No. 15/118,050, filed as application No. PCT/EP2015/074034 on Oct. 16, 2015, now Pat. No. 10,779,728.

(51) Int. Cl.
*A61B 3/13* (2006.01)
*A61B 3/14* (2006.01)
*A61B 3/117* (2006.01)

(52) U.S. Cl.
CPC ............ *A61B 3/13* (2013.01); *A61B 3/14* (2013.01); *A61B 3/1176* (2013.01)

(58) Field of Classification Search
CPC ............ A61B 3/1176; A61B 3/13; A61B 3/14
See application file for complete search history.

(56) References Cited

U.S. PATENT DOCUMENTS

2012/0211644 A1* 8/2012 Zheng ................. G01J 9/00
250/208.2

FOREIGN PATENT DOCUMENTS

CN 1737638 A * 2/2006

* cited by examiner

*Primary Examiner* — Jack Dinh

(57) ABSTRACT

A system and method for ophthalmic surgery in which a light field camera is used to capture a digital image of the surgical field including the eye. The digital image is used to create image information and directional information, which is then used to from a three dimensional (3D) image with motion parallax.

4 Claims, 3 Drawing Sheets

OPHTHALMIC SURGERY USING LIGHT-FIELD MICROSCOPY

TECHNICAL FIELD

The present disclosure relates to systems and methods for ophthalmic surgery.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Microscopic images are used in ophthalmic surgeries to view small eye structures. Although they are magnified, how closely these images otherwise match what can be seen with normal vision impacts how well the surgery can be performed. Monocular microscopic images provide information about the object being viewed through size, focus, shadowing and occlusion. Three dimensional (3D) displays have now added binocular disparity, the difference in how an image is seen by one eye as compared to the other, to the images, which makes them more realistic and provides additional visual information to the surgeon. However, there remains room for improvement in the information contained in microscopic images used in ophthalmic surgeries.

The present invention, in some aspects, uses motion parallax to provide additional visual information in ophthalmic surgical images. A typical person does not consciously distinguish motion parallax, but it provides important positional information in normal human vision that we use to navigate and manipulate objects accurately in three dimensions.

One easy way to understand motion parallax is to look at tree leaves of branches in a distance. Often it is difficult or impossible to tell which leaves and branches are closer and which are further away. However, if you move your head from side to side, it then becomes much easier to tell the relative distances. This ability to distinguish distance arises from motion parallax, which makes the closer leave and branches appear to move faster as you move your head. Most people take advantage of motion parallax by moving their head, intentionally or unintentionally, without ever consciously recognizing the visual clue it provides.

As the tree example above makes clear, motion parallax provides useful positional information even at a distance, but as FIG. 1 illustrates, it plays an even more significant role in obtaining visual information when objects are closer to the viewer. In fact, in the personal space where ophthalmic surgeries are performed "motion perspective" which is motion parallax, is roughly as important as binocular perspective in providing visual information about the position of an object, such as where a surgical instrument is in relation to an eye.

Despite the importance of information provided by motion parallax, it has not previously been incorporated into ophthalmic surgery systems, such as microscopes.

SUMMARY

The disclosed embodiments of the present disclosure provide a system for performing ophthalmic surgery. The system includes a magnifying lens through with light reflected from an eye undergoing ophthalmic surgery passes, a light field camera that receives light that has passed through the magnifying lens and that coverts the light to digital information, a processing resource that receives the digital information from the light field camera and creates image information and directional information from the digital information without using extrapolation, and a three dimensional (3D) visual display that receives the image information and directional information and uses it to display a 3D image of the eye.

In further embodiments, which may be combined with one another unless clearly mutually exclusive, the magnifying lens may include a direct contact lens or an indirect lens, the light field camera may include a microlens array and a photosensor configured such that the microlens array projects microimages onto the photosensor, the photosensor may include a pixel array and each pixel in the pixel array may receive light from only one microlens, the photosensor may include a pixel array and at least one pixel in the pixel array may receive light from at least two microlenses, the microlens array may be located at a focal point of the lens, the light field camera may further include a main lens and the microlens array may be located at a focal point of the main lens, the 3D visual display may include glasses or goggles, the 3D visual display may include a motion parallax-enabled screen, the motion parallax-enabled screen may include an auto stereoscopic display, the motion parallax-enabled screen may include a single screen display, the motion parallax-enabled screen may include a multiview display, and the system may include a second 3D display.

The present disclosure also provides a method of displaying a three dimensional (3D) image of an eye undergoing ophthalmic surgery. The 3D image includes motion parallax. The method includes producing plurality of microimages of the eye undergoing ophthalmic surgery using a microlens array in a light field camera, converting light in these microimages to digital information using a photodetector in the light field camera, creating image information and directional information from the digital information without using extrapolation, sending the image information and directional information to a 3D visual display, displaying a 3D image on the visual display, wherein the 3D image appears to move with motion parallax if a user viewing the 3D image on the visual display moves his or her head.

In further embodiments, which may be combined with one another unless clearly mutually exclusive, the method may also include displaying a second 3D image on a second visual display, wherein both 3D images have a frame of reference and the frame of reference for the first 3D image corresponds to the frame of reference of the first user with respect to the eye and the second 3D image corresponds to the frame of reference of the second user with respect to the eye, the second image may appear to move with motion parallax if the second user moves his or her head, the method may also include detecting a location of the user's head and adjusting the 3D image based on the detected location, the method may also include displaying a left eye display and a right eye display, the method may also include displaying the 3D image on a screen, and creating image information and directional information from the digital information may include running an algorithm on a processing resource to determine the color an intensity of light as well as a vector of light.

BRIEF DESCRIPTION OF THE DRAWINGS

For a more complete understanding of the present invention and its features and advantages, reference is now made to the following description, taken in conjunction with the accompanying drawings, in which.

DETAILED DESCRIPTION

The present disclosure relates to ophthalmic surgery, and more specifically, to systems for and methods using a light field camera during ophthalmic surgery. These systems and methods may produce a 3D microscopic image that exhibits motion parallax. They may also be used to produce an image accurately oriented for more than one point-of-view. These systems and methods may further be used to provide 3D data other than an image.

Figure 1:
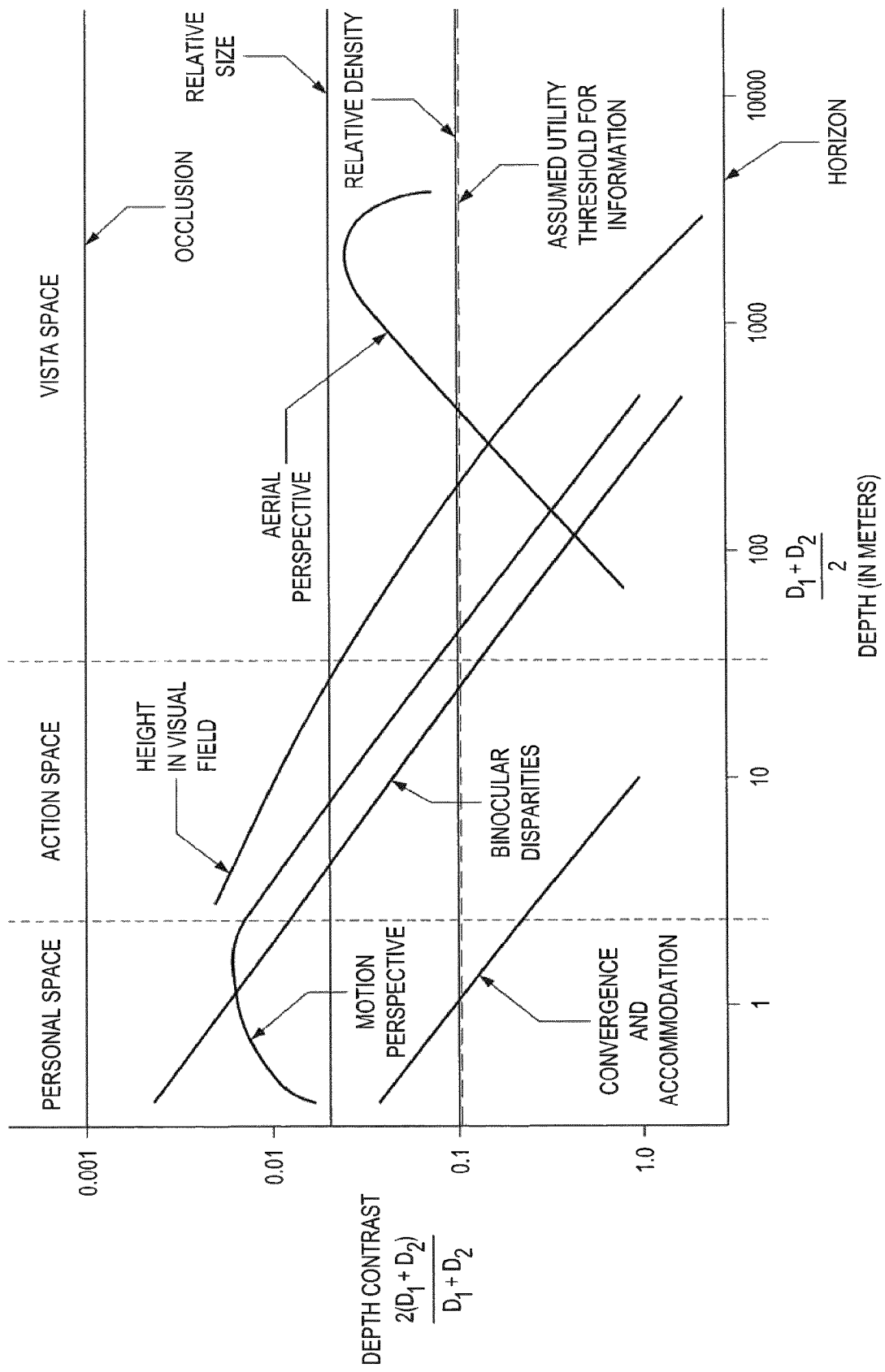
FIG. 1 is a prior art graph of the importance of components of visual information at various distances as illustrated in Cutting, J. E & Vishton, P. M., "Perceiving layout and knowing distances: The interaction, relative potency, and contextual use of different information about depth," In W. Epstein & S. Rogers (Eds.) Perception of space and motion, pp. 69-117, Academic Press, San Diego, Calif. (1995).
Figure 2:
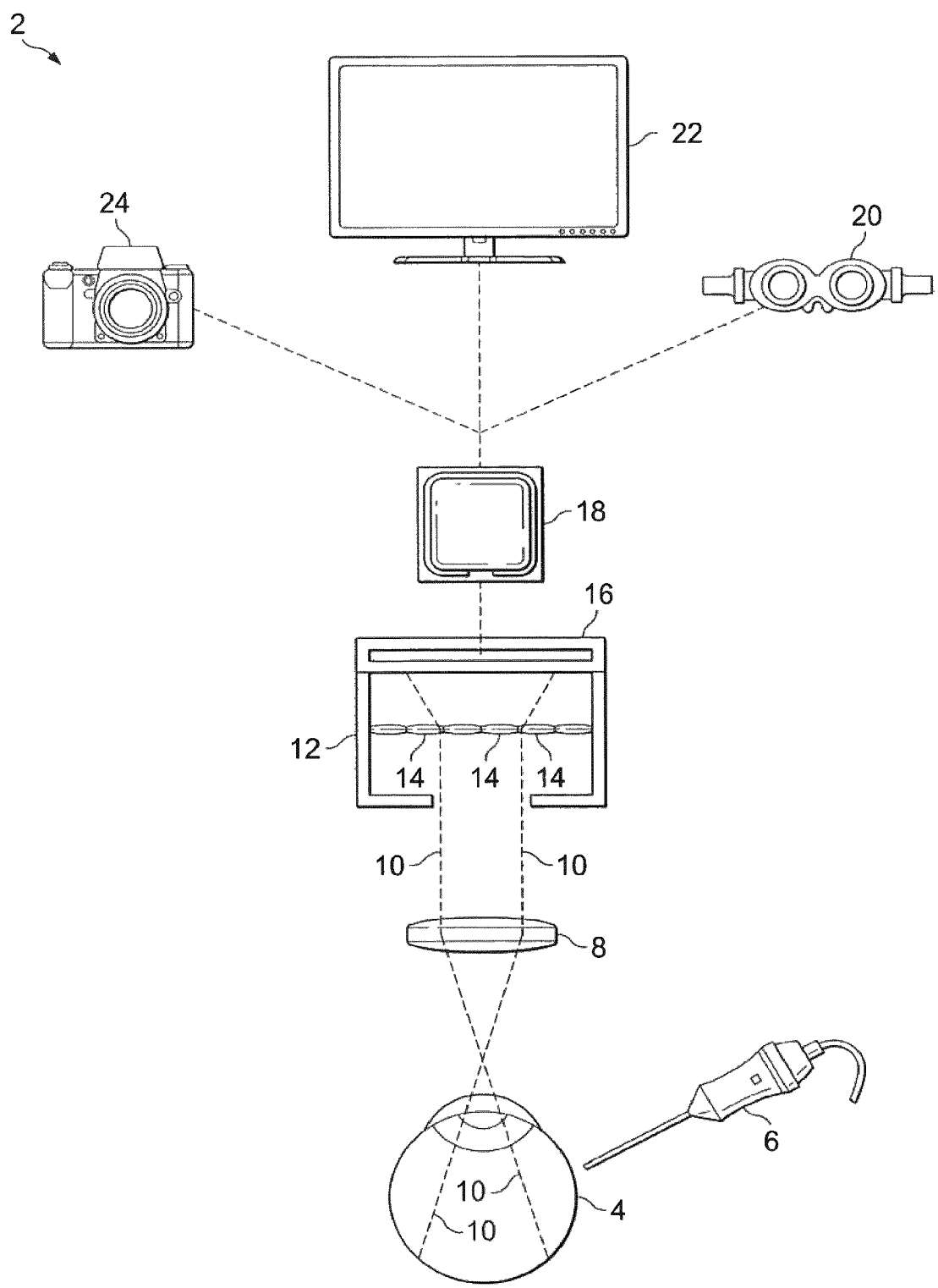
FIG. 2 is a schematic diagram of an ophthalmic surgical microscope system containing a light field camera.

FIG. 2 is a schematic diagram of an ophthalmic surgical microscope system 2 for performing ophthalmic surgery on an eye 4 using a surgical instrument 6. System 2 includes at least one magnifying lens 8 through with light beams 10 reflected from eye 4 pass before entering light field camera 12. Light field camera 12 includes microlens array 14 and photosensor 16, which capture light beams 10. Light field camera 12 provides digital information regarding captured light beams 10 to processing resource 18, which uses the digital information to display an image on a visual display device, typically a multiview display, such as 3D glasses or goggles 20 or parallax-enabled screen 22, or to sound an alarm, move surgical instrument 6 away from eye 4, or otherwise provide non-visual information or take mechanical action using non-visual output 24.

The ophthalmic surgery may include vitreoretinal surgery, other surgeries in which a surgical instrument enters the interior of the eye, such as the vitreous, cataract or vision corrections surgery, other surgeries in which a surgical instrument does not enter the interior of the eye, or any other eye surgery or procedure in which a magnified image of the eye is used or proximity of an instrument to the eye is detected.

Surgical instrument 6 may include cannulas, a light source, forceps, and scalpels.

Magnifying lens 8 may include any type of magnifying lens used in ophthalmic surgery, such as direct contact lenses and indirect lenses, including wide-view lenses. Although one lens 8 is shown in FIG. 2, multiple lenses may be used to allow the magnification or other aspects of the visual image to be changed. In some embodiments, magnifying lens 8 may be present in light field camera 12, or it may not be present at all. Particularly, because light field camera 12, in conjunction with processing resource 18, may change the focus of any visual image using data captured by microlens array 14, it may be possible for the visual image displayed on visual displays 20 and 22 to be magnified without using a magnifying lens 8.

Light beams 10 are reflected from eye 4 or surgical instrument 6 or another object in the surgical field. Light beams 10 may include visual spectrum light, but may also include light outside of the normal visual spectrum, which may be rendered into a visual spectrum representation or used for non-visual information.

Light field camera 12 may be any light field camera or other device or sensor able to capture information about the direction from which a light beam arrives and digitize that information, such that motion parallax may be included in a display created using the digital information. Typically light field camera 12 captures not only image information, such as light color and intensity, but also directional information regarding the vector of the light ray.

In light field camera 12, photosensor 16 may be any electronic device able to convert light to a digital image. For instance, it may be a digital camera, a light-to-digital sensor, a semiconductor charge-coupled device (CCD), a complementary metal-oxide-semiconductor (CMOS) device, an N-type metal-oxide-semiconductor (NMOS) device, or another electronic device containing an array of photodiodes as part of one or more integrated circuits.

Microlens array 14 includes any array of microlenses, each of which projects a separate microimage of the light that reaches that microlens onto photosensor 16. Thus, with an array of microimages, each image generated by a separate microlens, is converted by photosensor 16 into digital information. Photosensor 16 may include a pixel array (not shown). The pixel array and microlens array 14 may be arranged such that each pixel receives light from only one microlens, or each pixel may received light from more than one microlens, or some pixels may receive light from only one microlens, while other pixels receive light from more than one microlens. The distance between microlens array 14 and photosensor 16 and other aspects of their configuration may be as described in US 2012/0327222. Typically, microlens array will be placed at the focal plane of lens 8 or that of a main lens of light field camera 12.

Light field camera 12 may be one produced by Raytrix Gmbh (Germany), particularly the Raytrix R5, R11, and R29 cameras. Light field camera 12 may also be one produced by Lytro (US), particularly the Lytro ILLIUM®.

Processing resource 18 uses this digital information from photosensor 16 to produce image information and directional information. This directional information may be further used to generate a 3D image containing motion parallax information or to create non-visual information containing depth or movement information.

Processing resources 18 may be separate from and in communication with light field camera 12 or part of light field camera 12. Processing resource 18 will typically include or be in communication with a memory that stores one or more algorithms for processing digital information from photosensor 16 to generate the information usable to display a 3D image containing motion parallax on a visual display such as display 20 or 22, or to create non-visual information containing depth or movement information. Such algorithms may use information regarding the arrangements of components of light field camera 12, such as the arrangement of microlens array 14 with respect to photosensor 16, and the presence of any additional elements, in generating the information. Processing resource 18 may also use any algorithm developed for contexts other than ophthalmic surgery that is suitable for generating information usable to display a 3D image containing motion parallax on a visual display. Furthermore, processing resource 18 may use an algorithm suitable for also generating a two-dimensional (2D) visual display, or a 3D visual display without motion parallax.

Light field camera 12 may further include an aperture, additional lenses, or elements to assist with image capture.

Light field camera 12, in connection with processing resource 18, and optionally also in connection with one or more additional cameras, photosensors, or processing resources, may produce information usable to display a 3D image containing motion parallax information with sufficient resolution to be used in ophthalmic surgery.

3D glasses or goggles 20 may include any device worn on a user's head that is able to project different images to the left eye and right eye and to adjust the point of view of the image when the user's head moves. However, due to goggle fogging, at least the surgeon may instead use motion parallax-enabled screen 22, which may include any screen able to display a 3D image in such a manner that the perspective moves with a user, such as an auto stereoscopic display, a single screen display, or a multiview display. For instance, it may include an LCD screen with a lenticular imaging cover or a parallax barrier, which has precision slits or pinholes providing different images to the left eye and right eye, or an adaptive parallax barrier, adaptive masks, optimized for each image frame. Motion parallax-enabled screen 22 may be a 3D visual display produced by Raytrix, such as a Raytrix autostereoscopic display. Motion parallax-enabled screen 22 may be a 3D visual display produced by Lytos, such as the display on the Lyton ILLIUM® camera. If a single view stereoscopic display is used, then additional components to track the user's head may be included in system 2 so that the display may be adjusted based on movement. Visual displays may also include holographic or other displays, as they become compatible with ophthalmic surgery.

Although two visual display devices 20 and 22 and one non-visual output 24 are illustrated in FIG. 2, system 2 may have as few as only one visual display device or only one non-visual output, or it may have any number of visual display devices, any number of non-visual outputs, or any combinations thereof. Although visual display devices 20 and 22 are 3D visual display devices capable of displaying a 3D image with motion parallax, system 2 may also include one or more visual display devices able to display a 3D image without motion parallax, or one or more visual display devices able to display a 2D image.

Figure 3:
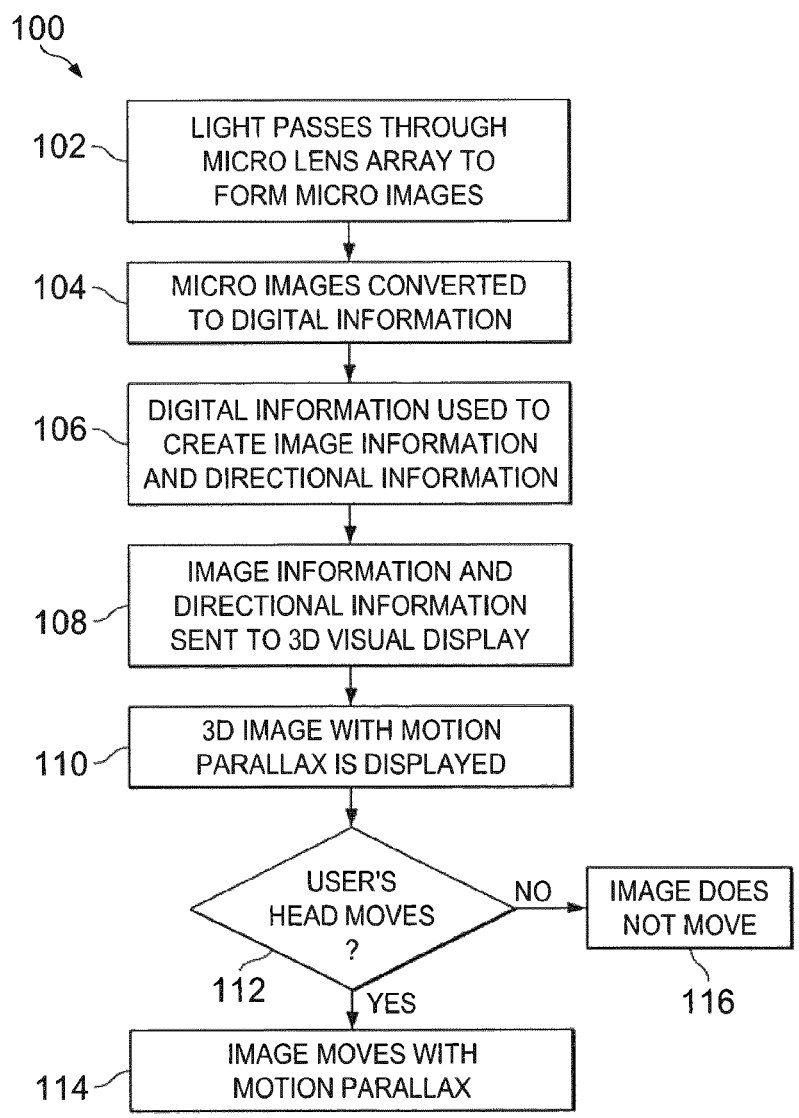
FIG. 3 is a flow chart of a method of displaying a 3D image with motion parallax of an eye undergoing an ophthalmic surgery.

FIG. 3 is a flow chart of a method of displaying a 3D image with motion parallax of an eye, such as eye 4, undergoing an ophthalmic surgery. In step 102, light passes through a microlens array of a light field camera to produce a plurality of microimages. In step 104, the light in these microimages is converted to digital information by the photodetector in the light field camera. In step 106, image information and directional information is created using this digital information. This image information and directional information is created without any extrapolation from the digital information. Although extrapolation may be acceptable in many contexts, in ophthalmic surgery the visual information must accurate, such that extrapolation is not acceptable. In step 108, this image information and directional information is sent to a 3D visual display. In step 110, a 3D image with motion parallax is displayed. In step 112, if a user moves his or her head, the image appears to move with motion parallax in step 114. If the user does not move his or her head, the image does not appear to move in step 116.

In step 102, the light passing through the microlens array may produce a plurality of microimages that each reach distinct portions of the photodetector. For instance, if the photodetector includes pixels, each pixel may receive light from only one microlens. Alternatively, the microimages may overlap at least partially on the photodetector, such that each pixel receives light from at least two microlenses. The arrangement between microlenses and the photodetector may be used in step 106 in creating image information and directional information.

Step 106 may include an algorithm usable to produce a 3D image containing motion parallax using light field camera data in other contexts. For instance, if may include an algorithm such as that disclosed in US 2012/0327222.

If, in step 112, the user moves his or her head, then when the image appears to move with motion parallax in step 114, this provides additional depth perception to the user. This movement with motion parallax may include perspective and occlusion pattern changes in the image. The additional depth perception may allow more accurate movements and better surgical instrument control during ophthalmic surgery.

If a multiview display is used, then separate left and right eye displays may form the 3D image displayed in step 110.

If a single view stereoscopic display is used to display the 3D image, then step 114 may further include tracking the position of the user's head and adjusting the image based on the user's head movements.

Furthermore, the method may also include displaying an additional 3D image with motion parallax to an additional user whose frame of reference is different from that of the first user. For instance, the first user may be a surgeon and the additional user may be a microscope technician. The second 3D image may be displayed from the correct frame of reference for all users. Conventional 3D image systems can only display the image from the correct frame of reference for one user. Furthermore, one user may move his or her head, while the others do not, or the users may move their heads in different manners, and the 3D image will display motion parallax accurately for each user.

The method may further include displaying a 2D image or a 3D image without motion parallax for an additional user, such as a technician who does not need depth information provided by motion parallax.

Furthermore, the method may include displaying an image using other capabilities of a light field camera. For instance, it may include displaying an image that is in focus no matter where the user is with respect to the object image. For instance, the image may be in focus regardless of how close the user is to the eye undergoing ophthalmic surgery. The image may also be in focus at various magnifications even if no magnifying lens is used to acquire the image.

The method may further include additional steps, such as using directional information to cause a change in a non-visual output. For instance, if directional information indicates that a surgical instrument is in an inappropriate position or near the eye, then the non-visual output may sound an alarm or even restrict further movement of the surgical instrument. Directional information and image information may be subjected to further algorithms, such as object detection algorithms, by a processing resource in order to provide these functions.

The method may further include sending directional information and image information or even the unprocessed digital information to a non-visual output that includes a memory so that a record of the ophthalmic surgery may be created.

These and other aspects of the method may be enabled by creating a 3D map of the surgical field using the light field camera.

The above disclosed subject matter is to be considered illustrative, and not restrictive, and the appended claims are intended to cover all such modifications, enhancements, and other embodiments which fall within the true spirit and scope of the present disclosure. For instance, although an ophthalmic surgical microscope is disclosed herein, other ophthalmic surgical visual devices may also incorporate the present teachings. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A method of displaying a three dimensional (3D) image of an eye undergoing ophthalmic surgery, the 3D image including motion parallax, the method comprising:

producing plurality of microimages of the eye undergoing ophthalmic surgery using a microlens array in a light field camera;

converting light in these microimages to digital information using a photodetector in the light field camera;

creating image information and directional information from the digital information without using extrapolation, wherein creating image information and directional information from the digital information comprises running an algorithm on a processing resource to determine the color and intensity of light as well as a vector of light;

sending the image information and directional information to a 3D visual display;

displaying a first 3D image on the visual display, wherein the 3D image appears to move with motion parallax if a user viewing the 3D image on the visual display moves his or her head; and comprising displaying a second 3D image on a second visual display, wherein a first frame of reference for the first 3D image corresponds to a frame of reference of the first user with respect to the eye, wherein a second frame of reference for the the second 3D image corresponds to the second frame of reference of the second user with respect to the eye, and wherein the second image appears to move with motion parallax if the second user moves his or her head.

2. The method of claim 1, further comprising detecting a location of the user's head and adjusting the 3D image based on the detected location.

3. The method of claim 1, further comprising displaying a left eye display and a right eye display.

4. The method of claim 1, further comprising displaying the 3D image on a screen.

* * * * *